US008602976B2

(12) United States Patent
Tulley

(10) Patent No.: US 8,602,976 B2
(45) Date of Patent: Dec. 10, 2013

(54) ENDOSCOPE

(75) Inventor: Matthew Tulley, Bamsley (GB)

(73) Assignee: Single Use Surgical Limited, Barnsley (GB)

( * ) Notice: Subject to any disclaimer, the term of this patent is extended or adjusted under 35 U.S.C. 154(b) by 309 days.

(21) Appl. No.: 12/947,098

(22) Filed: Nov. 16, 2010

(65) Prior Publication Data

US 2011/0118550 A1 May 19, 2011

(30) Foreign Application Priority Data

Nov. 17, 2009 (GB) .................................. 0920116.1
Jun. 21, 2010 (GB) .................................. 1010334.9

(51) Int. Cl.
*A61B 1/00* (2006.01)

(52) U.S. Cl.
USPC ............................ 600/149; 600/146; 600/150

(58) Field of Classification Search
USPC ......... 600/139–152, 104, 106, 107, 114–116, 600/131; 604/523–528; 606/1
See application file for complete search history.

(56) References Cited

U.S. PATENT DOCUMENTS

| | | | | |
|---|---|---|---|---|
| 5,007,406 | A | 4/1991 | Takahashi et al. | |
| 6,491,627 | B1 | 12/2002 | Komi | |
| 2004/0015054 | A1* | 1/2004 | Hino | 600/146 |
| 2007/0010801 | A1* | 1/2007 | Chen et al. | 606/1 |
| 2010/0069834 | A1* | 3/2010 | Schultz | 604/95.04 |

OTHER PUBLICATIONS

Search Report for United Kingdom Patent Application No. GB1010334.9 dated Sep. 8, 2010.

* cited by examiner

*Primary Examiner* — Matthew J Kasztejna
*Assistant Examiner* — Ryan Henderson
(74) *Attorney, Agent, or Firm* — James Creighton Wray

(57) ABSTRACT

An endoscope comprising a pulley, an insertion portion having a steerable section and a control wire connecting the pulley to the steerable section for controlling movement of the steerable section.

A portion of the control wire extends around the pulley, and the endoscope further comprises a cover for controlling slack in the wire. The cover is mounted on the pulley such that it is able to rotate with the pulley.

18 Claims, 9 Drawing Sheets

ENDOSCOPE

CROSS REFERENCE TO RELATED APPLICATIONS

This application claims priority from United Kingdom Patent Application No. 09 20 116.1, filed 17 Nov. 2009, and United Kingdom Patent Application No. 10 10 334.9, filed 21 Jun. 2010.

BACKGROUND OF THE INVENTION

1. Field of the Invention

The present invention relates to an endoscope and to a method of assembling an endoscope.

2. Description of the Related Art

Endoscopes containing control wires within Bowden cables that are pulled to steer a bending section at the distal end of the endoscope are well known. The loads in the controls wires are transferred to control wheels within a handle, and in a traditional endoscope this is achieved by a chain attached to the ends of the control wires passing over a sprocket attached to the control wheel. A problem with this arrangement is that it is expensive.

As an alternative it has been proposed to use wires directly attached to a pulley, but problems then exist with the management of the wires as they are unwrapped from, and rewrapped to, the pulley to ensure that they remain free from tangles.

BRIEF SUMMARY OF THE INVENTION

According to a first aspect of the present invention, there is provided an endoscope comprising a first pulley, an insertion portion having a steerable section and a control wire connecting said first pulley to said steerable section for controlling movement of said steerable section, wherein a portion of said control wire extends around said first pulley, and said endoscope further comprises a cover for controlling slack in the wire, said cover being mounted on said first pulley such that it is able to rotate with said first pulley.

According to a second aspect of the present invention, there is provided a method of assembling an endoscope comprising a pulley, an insertion portion having a steerable section and a control wife connecting said pulley to said steerable section for controlling movement of said steerable section, wherein said method comprises: locating a loop of said control wire around said pulley, and mounting a pulley cover over said loop of control wire and said pulley such that it is able to rotate with said pulley.

BRIEF DESCRIPTION OF THE SEVERAL VIEWS OF THE DRAWINGS

FIGS. 12A and 128 show two different perspective views of the pulley cover 12.

DETAILED DESCRIPTION OF THE PREFERRED EMBODIMENTS

FIG. 1

Figure 1:
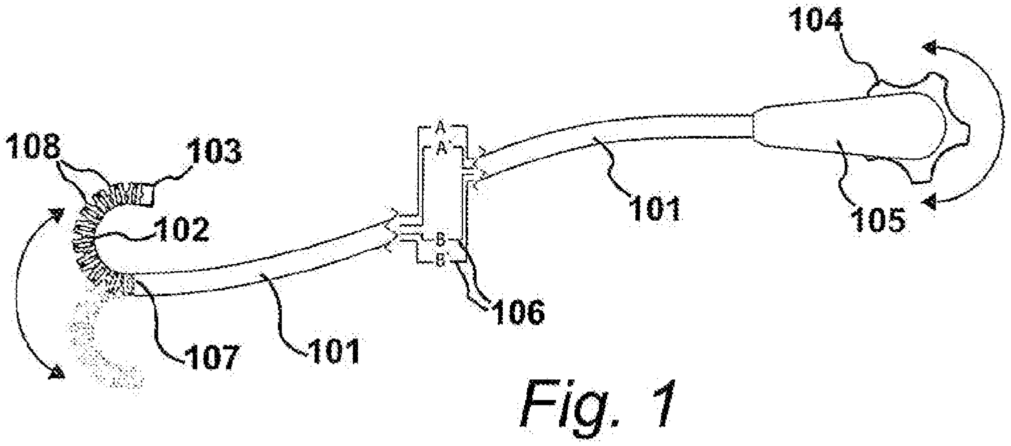
FIG. 1 shows an endoscope 100.

A typical endoscope 100 usable for diagnosis or therapy of celiac cavities of the body is shown in FIG. 1. The endoscope comprises insertion portion 101 having a steerable bending section 102 at one end. At the end of the bending section 102 is a distal cap 103 that contains a light source, camera and working channel through which instruments may be introduced during use.

A handle 105 is provided at the opposite end of the insertion portion 101. Two wheels 104 are provided on the handle 105 for controlling the bending section 102. Control wires 106 extend along the length of the insertion portion 101 through Bowden cables. The Bowden outers terminate at the proximal end 107 of the bending section. The control wires 106 pass through the rings 108 and are fixed to the distal cap 103.

During operation of the endoscope 100 the insertion length 101 is fed into the celiac cavity, using the steerable bending section 102 to navigate. The image from the camera is used when guiding the bending section by use of the control wheels 104 on the handle 105. The wheels control up, down, left and right movements by pulling on the control wires 106 that run through Bowden cables within the insertion length.

The principle of pulling on control wires to steer a bending section is well established in endoscopes. The loads on the wires can be high because of the forces required to move the colon, the forces required to bend the bending section, and the friction loss in the Bowden cables running back to the handle. These high loads must be transferred to the control wheel. As mentioned above, in a traditional endoscope this is achieved by a chain attached to the ends of the control wires passing over a sprocket attached to the control wheel. A simpler and lower cost alternative is to use the wires directly operating on a pulley.

FIGS. 2 to 5

Figure 2:
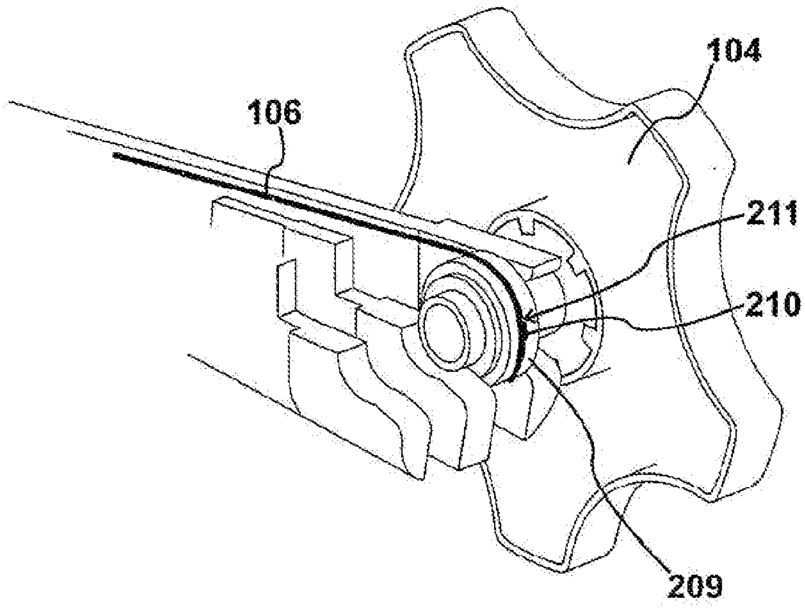
FIG. 2 shows a wheel 104 attached to a pulley 209 of the endoscope 100, and a wire 106 extending around the pulley.

An arrangement where the wire 106 is wound around a pulley 209 attached to the wheel 104 is shown in FIG. 2. (The outer casing of the handle has been removed in FIG. 2, along with a second pulley, for the purposes of clarity.) An anchor element 210 is rigidly fixed to a mid-point of the wire 106, and the anchor element resides within a hole 211 formed in the surface of the pulley, so that the wire is prevented from slipping around the pulley.

Figure 3:
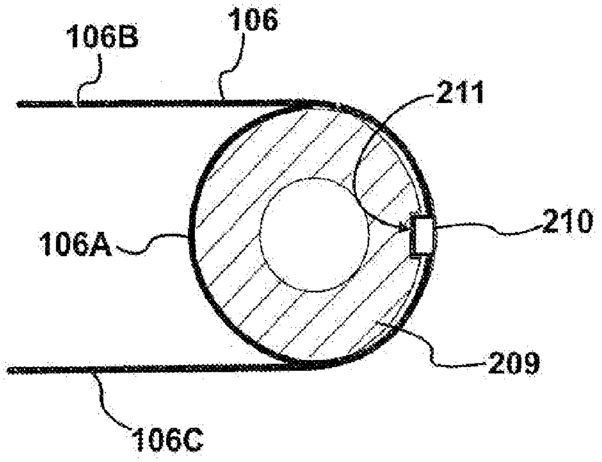
FIG. 3 shows a side view of the pulley 209 and wire 106.

The pulley 209 is shown in cross-section in FIG. 3 along with portions of the wire 106 in the vicinity of the pulley. As shown in FIG. 3, a portion 106A of the wire 106 is wrapped around the pulley for approximately 2.5 turns (900 degrees), while a second "up" portion 106B and a third "down" portion 106C of the wire 106 extend from the pulley 209. The anchor element 210 and the portion 106A of wire wrapped around the pulley 209 transfers the torque from the control wheel 104 to the wire 106.

A groove 312 is provided in the surface of the pulley 209 that extends around the pulley for approximately 90 degrees from each end of the hole 211 containing the anchor element 210. The groove 312 extends along a part of a helical curve around the pulley to assist with the management of the wire 106 as it coils onto and uncoils from the pulley 209.

Figure 4:
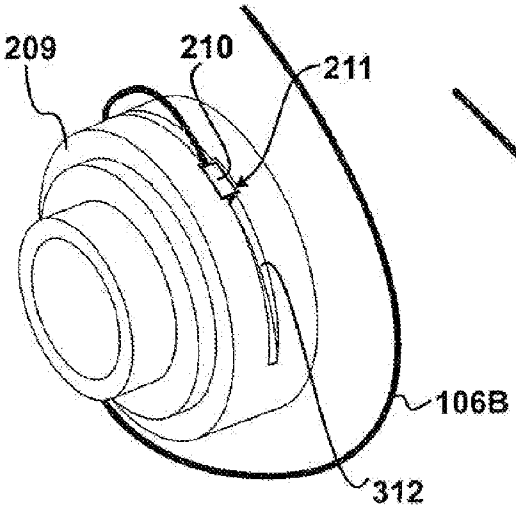
FIG. 4 shows the pulley 209 with a slack wire 106B.

Under low loads both portions 106B and 106C of wires extending from the pulley (e.g. both "up" and "down" wires) will be tight. As loads increase however, the tight wire tends to stretch, and so the system will produce slack. FIG. 4 shows the second "up" portion 106B of the wire having become slack, and consequently it is tending to unwind from the pulley 209. Because the wire is springy, when slack the radius of curvature of the wire increases more than the radius of the pulley and so the wire can move in unpredicted ways and later become tangled in the mechanism.

Figure 5:
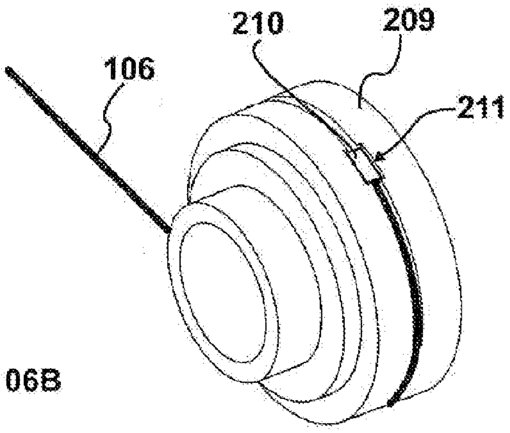
FIG. 5 shows the pulley 209 with the wire 106 when under tension.

In contrast, FIG. 5 shows the third "down" portion 106C wire 106, which is tight, close to the pulley 209, and not likely to tangle.

FIG. 6

Figure 6:
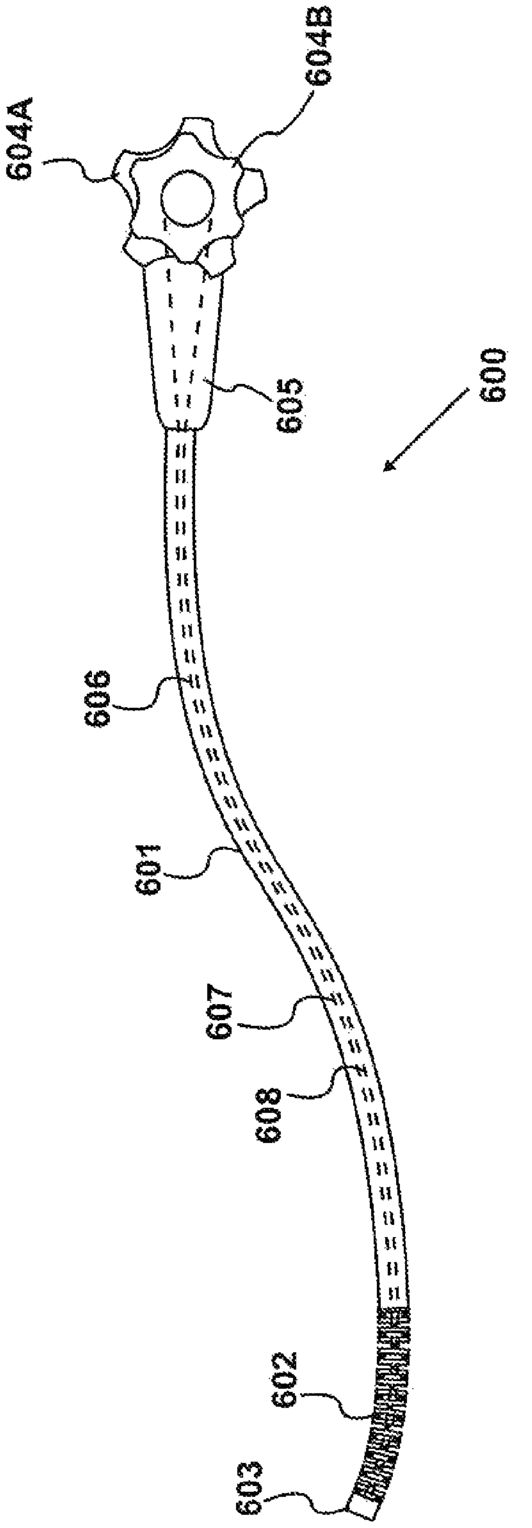
FIG. 6 shows an endoscope 600 embodying the present invention.

An endoscope 600 embodying the present invention is shown in FIG. 6. The endoscope 600 like the endoscope 100 is usable for diagnosis or therapy of celiac cavities of the body and it shares many of its features with endoscope 100. Thus, the endoscope 600 comprises an insertion portion 601 having a steerable bending section 602 at one end. At the end of the bending section 602 is a distal cap 103 that contains a light source, camera and working channel through which instruments may be introduced during use.

A handle 605 is provided at the opposite end of the insertion portion 601. Two wheels 604A and 604B are provided on the handle 605 that control the bending section 602. Control wires (such as wire 606, comprising portions 607 and 608) extend along the length of the insertion portion 601 through Bowden cables. The wheels 604A and 604B respectively control up-down, and left-right movements by pulling on the control wires.

FIG. 7

Figure 7:
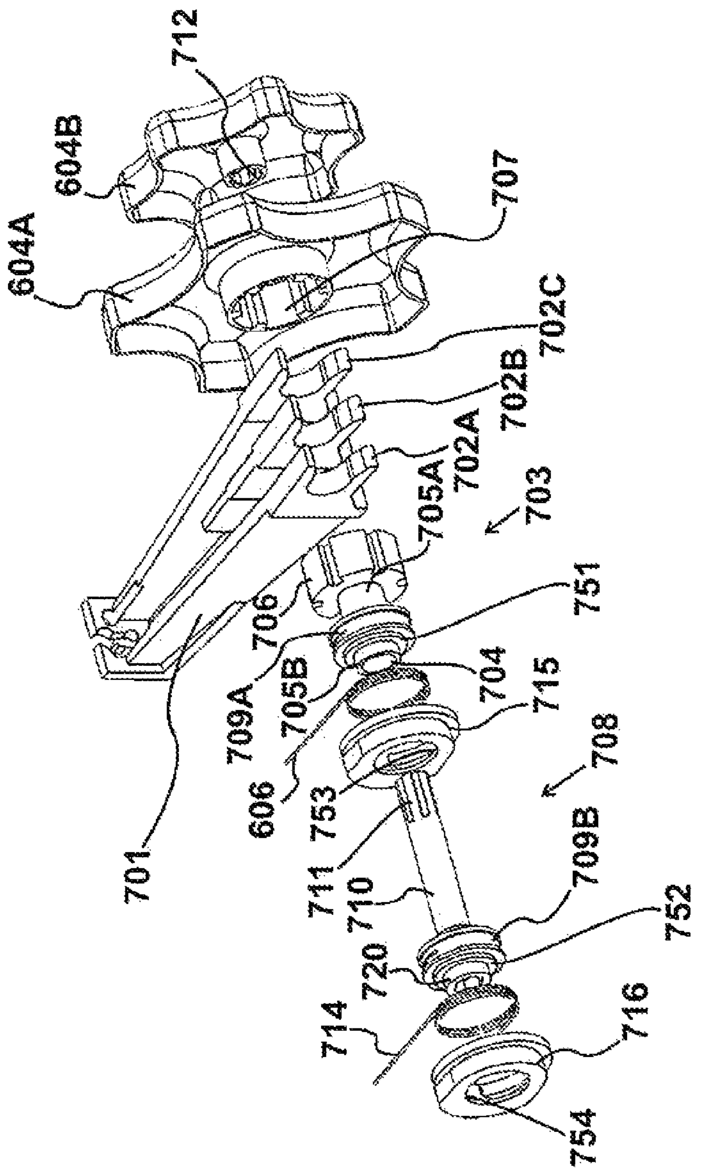
FIG. 7 shows an exploded view of internal components of the endoscope handle 105.

An exploded view illustrating internal components of the endoscope handle 105 is shown in FIG. 7. The handle 105 comprises a frame 701 defining bearings 702A, 702B and 702C, which each have an internal bearing surface extending cylindrically around a common axis. The bearings 702A, 702B and 702C are C-shaped, being open for almost 180 degrees about the common axis to allow other components of the handle to be clipped into place.

The endoscope handle also comprises a first pulley member 703 defining a cylindrical bore 704, a first pulley 709A, a slotted head 706, a middle shaft portion 705A and an end shaft portion 705B. The two shaft portions 705A and 705B are arranged either side of the pulley 709A, and each have a cylindrical surface that is concentric with the bore 704 and has a diameter configured to be a good fit within the bearing 702C, 702B respectively.

The first wheel 604A has a hole 707 defining splines, and the slotted head 706 is configured to be a good fit within the hole 707.

The endoscope handle further comprises a second pulley member 708 defining a second pulley 709B between an end shaft portion 720 and a central shaft 710, which has a grooved portion 711 at its end.

The central shaft 710 has a cylindrical outer surface configured to be a good fit within the bore 704 of the first pulley member 703, such that the two pulley members are able to rotate freely with respect to each other about the aforementioned common axis.

The end shaft portion 720 also has a cylindrical surface and it is configured to fit in the bearing 702A.

The second wheel 604B has a hole 712 defining splines configured to be a good fit on the grooved end portion 711 of the second pulley member 708.

Portions of the two control wires 606 and 714 are shown in FIG. 7 formed with loops configured to fit around the pulleys 709A and 709B respectively. (It should be understood that only portions of the wires in the vicinity of the pulleys are shown, and that the wires extend to the distal cap as indicated in FIG. 6.) In the present example, the wires 606 and 714 extend around the pulleys 709A and 709B for approximately three and a half turns. As described above with respect to FIGS. 2 and 3, the wires are provided with an anchor element that slots into a suitably dimensioned hole in the surface of the pulley. In the present embodiment, each of the anchor elements comprises a metal object that is attached to the respective wire by crimping.

The first pulley member 703 also defines a first cylindrical shoulder 751 between the first pulley 709A and the end shaft portion 705B. Similarly, the second pulley member 708 also defines a second cylindrical shoulder 752 between the second pulley 709B and the end shaft portion 720.

In accordance with the present invention, the handle also comprises pulley covers, 715 and 716, which will be described in detail below. The pulley covers 715 and 716 are dimensioned to be a good fit over a respective one of the pulleys 709A and 709B when the wires 606 and 714 are located about the pulleys. Furthermore, the pulley covers 715 and 716 are provided with respective circular apertures 753 and 754 configured to receive the first and second cylindrical shoulders 751, 752 respectively.

FIG. 8

To assemble the endoscope 600, the wire 606 is formed into loops that are then located about the pulley 709A, before the pulley cover 715 is located over the pulley and wire assembly. At the same time, the first cylindrical shoulder 751 of the pulley member 703 is located within the circular aperture 753 formed in the pulley cover 715.

Similarly, wire 714 is formed into loops that are then located about the pulley 709B. The second pulley cover 716 is then located over this second pulley and wire assembly, and the cylindrical shoulder 752 of the second pulley member 708 is located within the circular aperture 754 formed in the second pulley cover 716.

Figure 8:
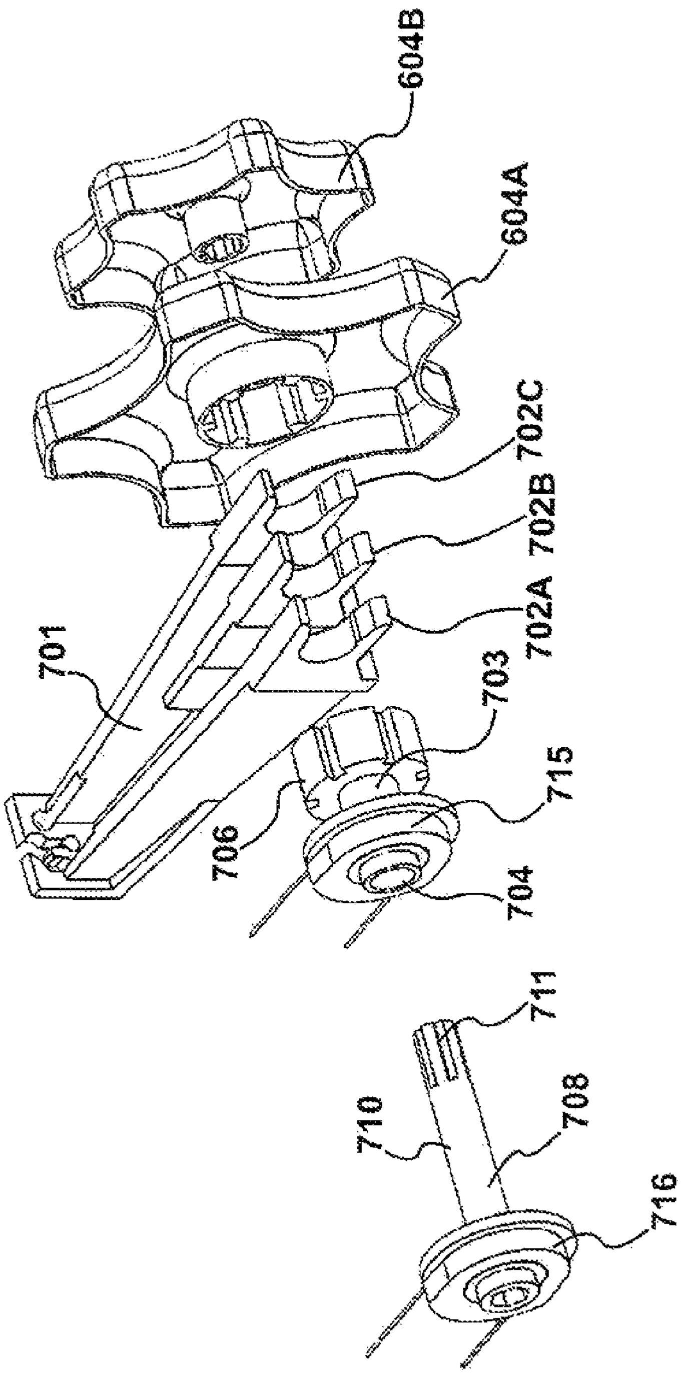
FIG. 8 shows the components of FIG. 7 after pulley covers 715 and 716 have been located on the pulley members 703, 708.

The components of FIG. 7 are shown again in FIG. 8 after pulley covers have been located on the pulley members in this way.

The central shaft 710 of the second pulley member 708 is then passed through the bore 704 of the first pulley member 703 and this assembly is clipped into the bearings 702A, 702B and 702C of the frame 701.

The handle 604A is then fitted to the slotted head 706 of the first pulley member 703 and the second handle 604B is fitted to the grooved end portion 711 of the central shaft 710.

Figure 9:
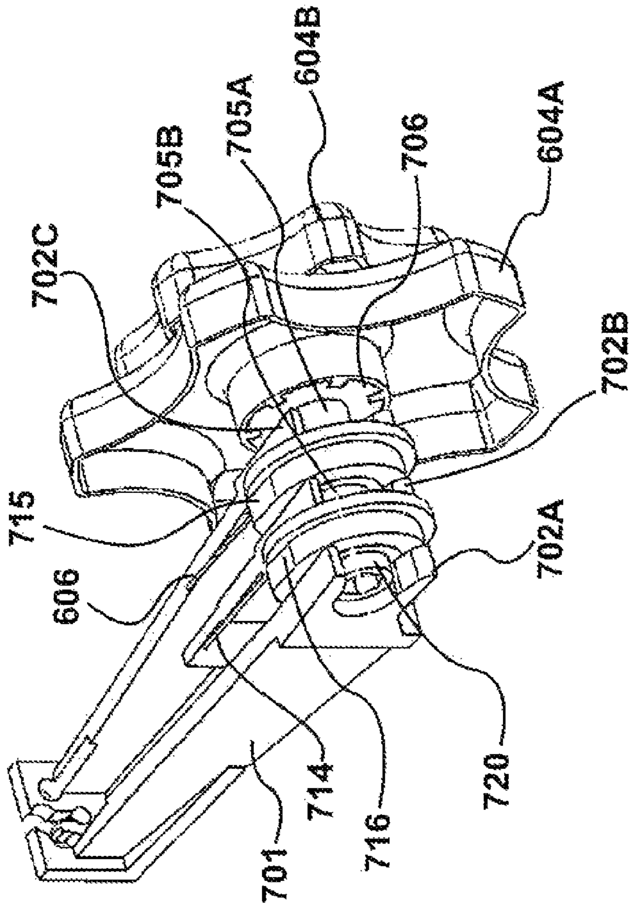
FIG. 9 shows a perspective view of the components previously shown in FIGS. 7 and 8 after assembly.
Figure 10:
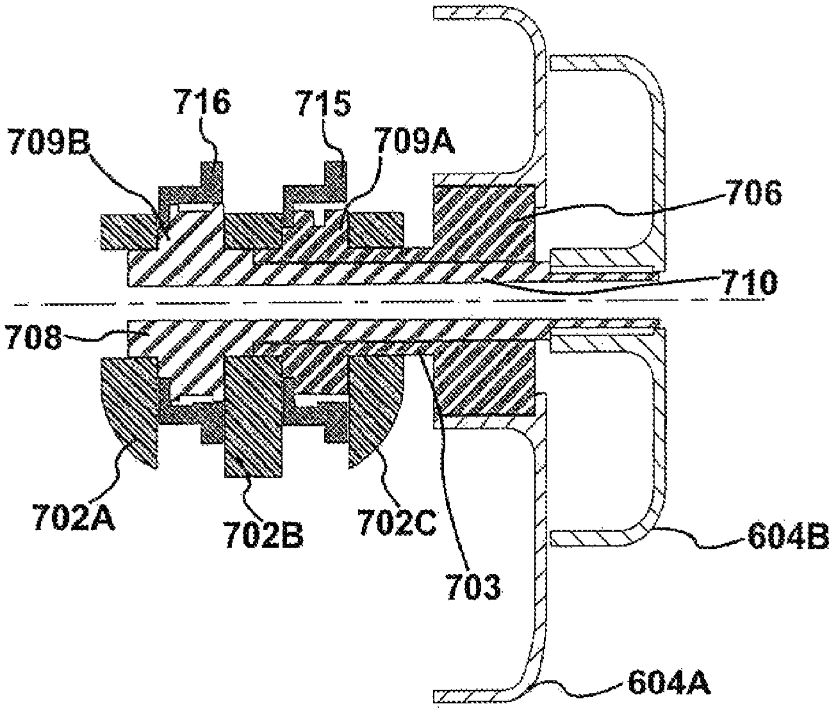
FIG. 10 shows a cross-sectional view of the components previously shown in FIGS. 7 and 8 after assembly.

FIGS. 9 and 10

The components previously shown in FIGS. 7 and 8 are shown after assembly in the perspective view of FIG. 9 and cross-sectional view of FIG. 10.

Control wheel 604B is used for 'left/right' control, and is connected to pulley 709B covered by pulley cover 716. Control wheel 604A is used for up/down control and is connected to the pulley 709A covered by pulley cover 715.

As illustrated by FIGS. 9 and 10, the pulley members are mounted to rotate within the frame 701. The first pulley member 703 having shaft portions 705B and 705A mounted within the bearings 702B and 702C, while the second pulley member 708 has the end shaft portion 720 mounted within the bearing 702A and the central shaft 710 mounted within the bore of the first pulley member 703.

In the present embodiment, the frame 701, the two pulley members 703 and 708, the pulley covers 715 and 716 and the wheels 604A and 604B are each moulded from a plastics material. Furthermore, the use of a chain and sprocket arrangement for connecting the wheels to the control wires is avoided by attaching the control wires directly to the pulleys. Consequently, the endoscope has a low cost construction allowing it to be used once and then disposed of, thereby avoiding contamination/sterilisation problems associated with the re-use of endoscopes.

FIG. 11

Figure 11:
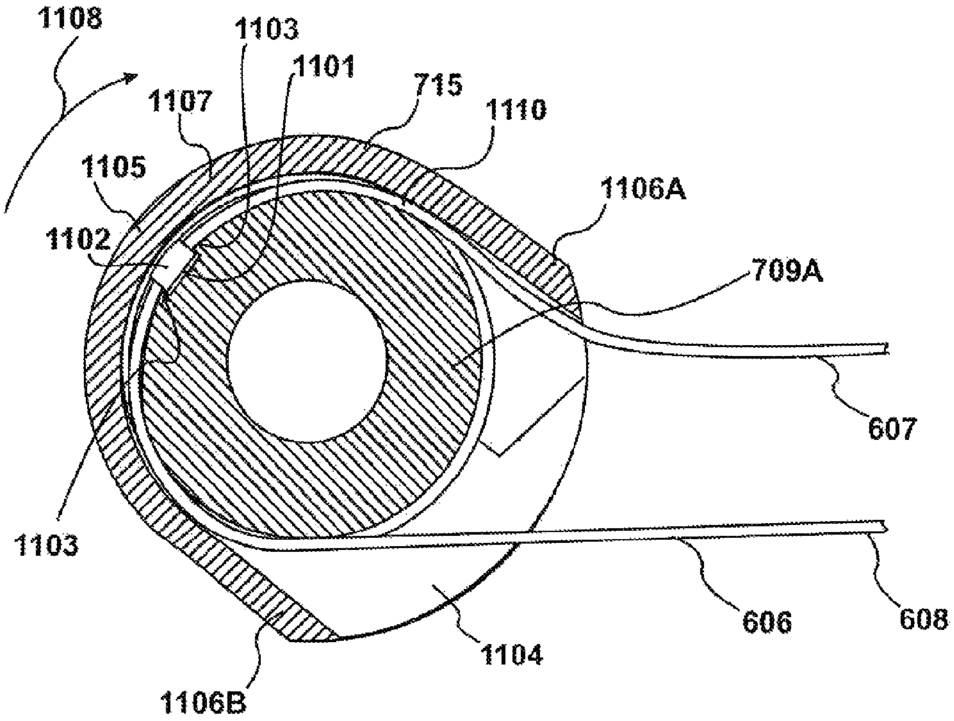
FIG. 11 shows the pulley cover 715 located on the pulley 709A.

The pulley cover 715 located on the pulley 709A is shown in FIG. 11. For the purposes of clarity, FIG. 11 shows the wire 606 simply looped around the pulley 709A for approximately a half turn. However, in a preferred embodiment the wire is looped around the pulley approximately three and a half times in a helical manner.

As described above, the pulley 709A defines a hole 1101 configured to receive an anchor element 1102 that is rigidly attached to the wire 606. A groove 1103 extends partly around the pulley from either end of the hole 1101, so that a portion of the wire 606 on either side of the anchor element 1102 resides within the groove 1103.

The pulley cover 715 has a surface 1104 from which a side wall 1105 extends at right angles. The side wall comprises two substantially straight arms 1106A and 1106B joined by a curved central portion 1107 that extends approximately 180 degrees around a circle. The curved central portion of the wall has an inner surface configured to fit around the outside of the pulley 709A and wire 606.

The pulley cover 715 fits over the pulley 709A and can turn freely on the pulley. At the rear of the pulley in the vicinity of the anchor element 1003 the pulley cover 715 fits closely over the pulley 709A, so constraining the wire 606 in the groove 1103. When the pulley is turned in the direction of the arrow 1108 the lower portion 608 of the wire 606 is placed in tension and is therefore straight and keeps in the pulley's groove 1103. The slack side of the wire 606, that is the upper portion 607, within the pulley cover 715 tends to expand (as described previously with respect to FIG. 4) and presses against the inside of the pulley cover. As the pulley is turned, frictional forces between the slack expanded portion 607 of the wire and the pulley cover 715 cause the pulley cover to turn with the pulley, so that the arm 1106A of the pulley cover presses against the slack portion 607 of the wire. The pulley cover continues to turn with the pulley until the slack is taken up, when the wire portion 607 pushes back on the arm 1106A of the pulley cover to give a torque (in this case anticlockwise) matching the friction force (clockwise) from the slack wire within the pulley cover. In this way, the amount the pulley cover turns depends on the amount of slack to be taken up (which depends on the force on the 'tight' wire and the amount it stretches).

In this way, the pulley cover 715 located on the pulley 709A constrains the wire 606 in the pulley groove 1103 and manages the slack wire (in the present example the upper portion 607) to prevent the tangling.

It should be understood that when the pulley 709A is rotated in the opposite sense to arrow 1108, the upper portion 607 of the wire 606 will become tight and the lower portion 608 of the wire will become slack. Consequently the coiled part of the lower portion 608 around the pulley 709A will tend to expand away from the pulley and push against the inside of the pulley cover 715. As a result the pulley cover will be pushed by frictional forces as described above such that the arm 1106B pushes against the lower portion 608 to take up the slack.

It should also be understood that the second pulley cover 716 operates on the wire 714 on the second pulley 709B to perform a similar function.

Figure 12A:
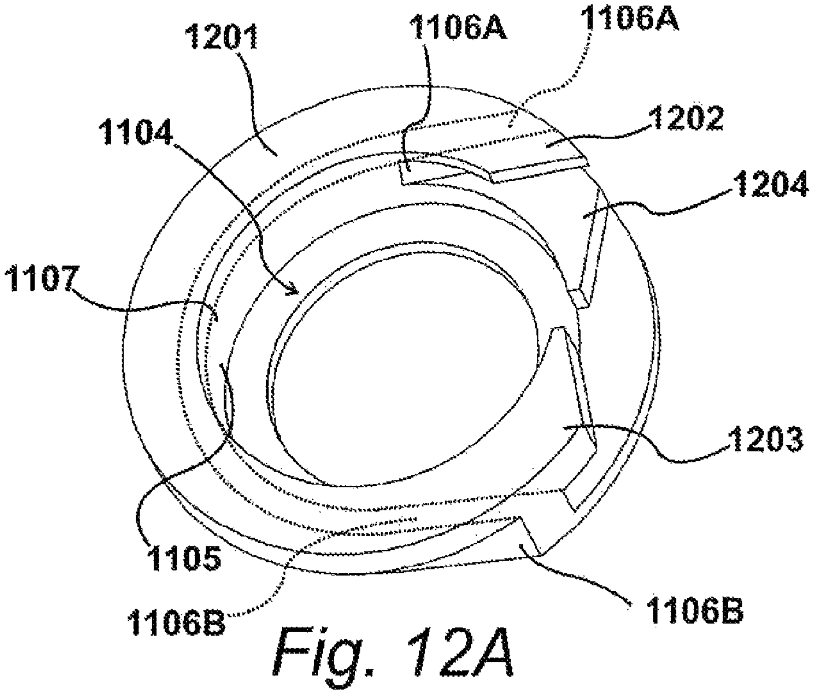
Figure 12B:
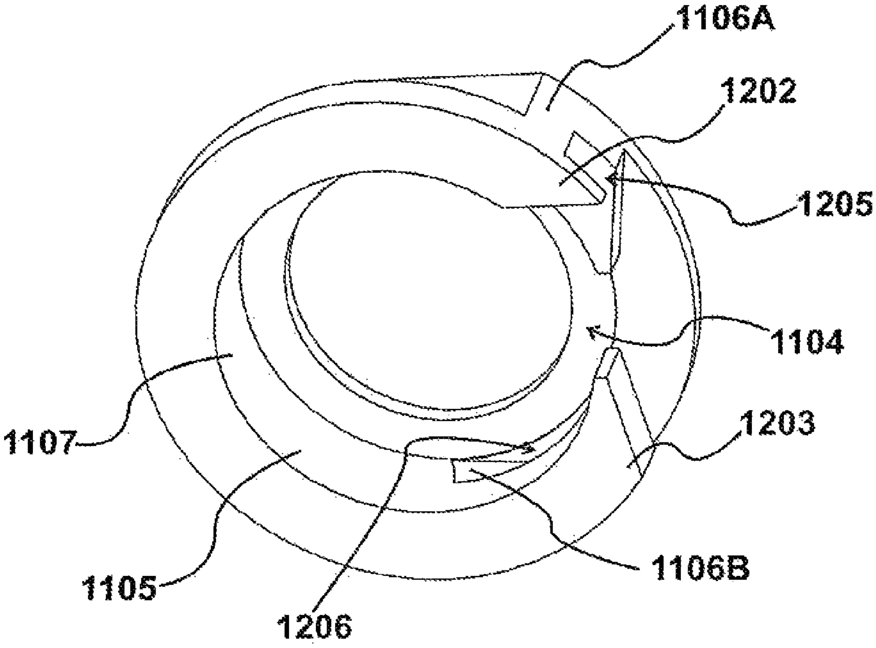

FIGS. 12A and 12B

The pulley cover 715 is shown in the perspective views of FIGS. 12A and 12B. As mentioned above, the side wall 1105, which extends from the surface 1104, has a curved central portion 1107 connecting two substantially straight arms 1106A and 1106B, which provide a force on the slack side of the wire 606 when the pulley 709A is rotated. In FIGS. 12A and 12B the arms (1106A and 1106B) are obscured by a flange 1201 and so the arms have been indicated in dotted outline in FIG. 12A.

As indicated in FIG. 11, the arms 1106A and 1106B define a gap between which the wire extends from the pulley towards the steerable bending section 602 (shown in FIG. 6). However, as shown in FIGS. 12A and 12B, the cover 715 also defines guide plates for maintaining the wire 606 in the correct planes. First and second, upper guide plates 1202 and 1203 extend from the arms 1106A and 1106B respectively, and a lower guide plate 1204 extends from the arm 1106A. The first upper guide plate 1202 and lower guide plate 1204 are arranged to form a first slot 1205 such that the arm 1106A forms the bottom of the slot. The second upper guide plate 1203 and the surface 1104 form a second slot 1206 such that the arm 1106B forms the bottom of the slot. During operation, the wire 606 extends from the pulley 709A through the slots 1205 and 1206.

It may be noted that the slots 1205 and 1206 are arranged to be at differing distances from the surface 1104. This is because the portion of the wire that is wrapped around the pulley forms a helical shape, and so the wire leaves the pulley at differing positions along the aforementioned common axis.

The invention claimed is:

1. An endoscope comprising a first pulley, an insertion portion having a steerable section and a control wire connecting said first pulley to said steerable section for controlling movement of said steerable section, wherein a portion of said control wire extends around said first pulley, and said endoscope further comprises a cover for controlling slack in the wire, said cover being mounted on said first pulley such that in dependence of forces applied to said cover by said wire:

(i) said cover is able to rotate with said first pulley; and (ii) said first pulley is able to rotate with respect to said cover wherein said first pulley has a circular edge and the cover has a wall extending around a part of the circular edge of said first pulley, such that a portion of said wire extends between said first pulley and said wall.

2. The endoscope according to claim 1 wherein the wire extends from said steerable section around said first pulley and back to said steerable section.

3. The endoscope according to claim 2 wherein an anchor element is fixed to said wire and said first pulley defines a recess for receiving said anchor element, such that rotation of the first pulley moves said anchor element and said anchor element moves said wire.

4. The endoscope according to claim 3 wherein said anchor element is crimped onto said wire.

5. The endoscope according to claim 2 wherein a said cover defines a first arm and a second arm, said first arm being configured to press against a first portion of said wire when the first pulley is rotated in a first direction, and said second arm being configured to press against a second portion of said wire when the first pulley is rotated in a second direction opposite from said first direction.

6. The endoscope according to claim 1 wherein said first pulley defines a groove around its circular edge and a portion of said wire extends along said groove.

7. The endoscope according to claim 6 wherein said groove follows a helical shape to facilitate helical coiling of said wire around said first pulley.

8. The endoscope according to claim 7 wherein: the wire extends from said steerable section around said first pulley within said groove and back to said steerable section; an anchor element is fixed to said wire; and said first pulley defines a recess for receiving said anchor element, such that rotation of the first pulley moves said anchor element and said anchor element moves said wire.

9. The endoscope according to claim 6 wherein: the wire extends from said steerable section around said first pulley within said groove and back to said steerable section; an anchor element is fixed to said wire; and said first pulley defines a recess for receiving said anchor element, such that rotation of the first pulley moves said anchor element and said anchor element moves said wire.

10. The endoscope according to claim 6 wherein the wire extends from said steerable section around said first pulley and back to said steerable section.

11. The endoscope according to claim 1 wherein a said cover defines a first arm and a second arm, said first arm being configured to press against a first portion of said wire when the first pulley is rotated in a first direction, and said second arm being configured to press against a second portion of said wire when the first pulley is rotated in a second direction opposite from said first direction.

12. The endoscope according to claim 11 wherein said cover defines a slot adjacent to each said arm, and said wire extends through said slots.

13. The endoscope according to claim 1 wherein said first pulley forms part of a first pulley member defining a cylindrical shoulder adjacent to said first pulley and said pulley cover defines a circular aperture in which said cylindrical shoulder resides.

14. The endoscope according to claim 1 wherein said endoscope comprises a second pulley to which a second wire is attached and a second pulley cover for controlling slack in the second wire, said second pulley cover being mounted on said second pulley such that said cover is able to rotate with said second pulley and said second pulley is able to rotate with respect to said cover, in dependence of forces applied to said second pulley cover by said second wire.

15. The endoscope according to claim 14 wherein said second pulley forms a part of a pulley member that further comprises a cylindrical shaft fixed to said second pulley and said first pulley is mounted to rotate on said cylindrical shaft.

16. The endoscope according to claim 1 wherein: said first pulley defines a groove around its circular edge; the wire extends from said steerable section around said first pulley within said groove and back to said steerable section; an anchor element is fixed to said wire; and said first pulley defines a recess for receiving said anchor element, such that rotation of the first pulley moves said anchor element and said anchor element moves said wire.

17. The endoscope according to claim 1 wherein: said first pulley defines a helical shaped groove around its circular edge; the wire extends from said steerable section around said first pulley within said groove and back to said steerable section; an anchor element is fixed to said wire; and said first pulley defines a recess for receiving said anchor element, such that rotation of the first pulley moves said anchor element and said anchor element moves said wire.

18. An endoscope comprising a first pulley, an insertion portion having a steerable section, a control wire connecting said first pulley to said steerable section for controlling movement of said steerable section, and a cover for controlling slack in the wire, wherein a portion of said control wire extends around said first pulley, said first pulley has a circular edge and the cover has a wall extending around a part of said circular edge, such that a portion of said wire extends between said first pulley and said wall, said cover defines a first arm and a second arm, said first arm being configured to press against a first portion of said wire when the first pulley is rotated in one direction, and said second arm being configured to press against a second portion of said wire when the first pulley is rotated in a second direction opposite from said first direction, said cover is mounted on said first pulley such that, in dependence of forces applied to said cover by said wire:

(i) said cover is able to rotate with said first pulley; and (ii) when one of said first arm and said second arm presses against said wire, said first pulley is able to rotate with respect to said cover.

* * * * *